United States Patent
Flemmig et al.

(10) Patent No.: US 7,083,411 B2
(45) Date of Patent: Aug. 1, 2006

(54) TOOTH CLEANING POWDERS AND METHODS OF USE THEREOF

(75) Inventors: Thomas Flemmig, Muenster (DE); Bernd Gangnus, Andechs (DE); Oswald Gasser, Seefeld (DE); Rainer Guggenberger, Herrsching (DE); Ingo Haeberlein, Weilheim (DE); Bettina Windmmueller, Gilching (DE)

(73) Assignee: 3M Espe AG, Seefeld (DE)

( * ) Notice: Subject to any disclaimer, the term of this patent is extended or adjusted under 35 U.S.C. 154(b) by 306 days.

(21) Appl. No.: 10/239,647

(22) PCT Filed: Mar. 15, 2001

(86) PCT No.: PCT/EP01/02893

§ 371 (c)(1),
(2), (4) Date: Jan. 16, 2003

(87) PCT Pub. No.: WO01/72273

PCT Pub. Date: Oct. 4, 2001

(65) Prior Publication Data

US 2004/0091429 A1   May 13, 2004

(30) Foreign Application Priority Data

Mar. 24, 2000   (DE) ................ 100 14 416

(51) Int. Cl.
*A61C 3/02* (2006.01)
*C09K 3/14* (2006.01)
*A61K 8/00* (2006.01)

(52) U.S. Cl. ............... 433/88; 51/308; 424/49

(58) Field of Classification Search ............ 433/88
See application file for complete search history.

(56) References Cited

U.S. PATENT DOCUMENTS

| | | | |
|---|---|---|---|
| 3,882,638 A | | 5/1975 | Black |
| 3,892,843 A | | 7/1975 | Muhler et al. |
| 3,966,863 A | * | 6/1976 | Forward et al. .......... 424/52 |
| 4,082,841 A | * | 4/1978 | Pader ...................... 424/50 |
| 4,214,871 A | | 7/1980 | Arnold |
| 4,370,136 A | | 1/1983 | Widman et al. |
| 4,910,014 A | | 3/1990 | Nakagawa |
| 4,937,066 A | | 6/1990 | Vlock |
| 5,094,845 A | | 3/1992 | Vlock |
| 5,165,914 A | | 11/1992 | Vlock |
| 5,203,698 A | | 4/1993 | Blake et al. |
| 5,206,010 A | * | 4/1993 | Inoue et al. ............ 424/49 |
| 5,334,019 A | | 8/1994 | Goldsmith et al. |

(Continued)

FOREIGN PATENT DOCUMENTS

AU        54605        11/1983

(Continued)

OTHER PUBLICATIONS

International Search Report.

*Primary Examiner*—Cary E. O'Connor
(74) *Attorney, Agent, or Firm*—Crowell & Moring LLP

(57) ABSTRACT

Fine-grained powders or powder mixtures can be used to provide for spray cleaning of supragingival tooth surfaces. The abrasion of the tooth surface by the spraying of powder does not exceed 0.15 $mm^3$ in relation to a tooth surface of 10 $mm^2$ during a spray period lasting 2 minutes at a pressure of 4 bars and a distance of no more than 2.5 mm between the tooth surface and nozzle of the spray jet.

29 Claims, 1 Drawing Sheet

U.S. PATENT DOCUMENTS

| | | | |
|---|---|---|---|
| 5,645,841 A | 7/1997 | Hill et al. | |
| 5,651,959 A | 7/1997 | Hill et al. | |
| 5,665,374 A | 9/1997 | Hill et al. | |
| 5,865,620 A * | 2/1999 | Kutsch | 433/88 |
| 6,132,702 A * | 10/2000 | Witt et al. | 424/53 |
| 6,342,207 B1 | 1/2002 | Stoor et al. | |
| 6,648,644 B1 | 11/2003 | Flemming et al. | |

FOREIGN PATENT DOCUMENTS

| | | |
|---|---|---|
| DE | 29 30 836 | 2/1980 |
| DE | 36 31 799 C2 | 3/1988 |
| DE | 40 21 071 C2 | 1/1991 |
| DE | 37 26 349 C2 | 8/1996 |
| DE | 199 10 559 | 9/2000 |
| DE | 199 26 728 | 12/2000 |
| EP | 0 267 994 A1 | 5/1988 |
| EP | 0 035 040 A1 | 9/1991 |
| EP | 0 528 756 B1 | 9/1995 |
| GB | 988 513 A | 4/1965 |
| GB | 1 480 594 A | 7/1977 |
| JP | 03 271215 | 12/1991 |
| WO | WO 95/34275 | 12/1995 |
| WO | WO 00 53154 A | 10/2001 |

* cited by examiner

TOOTH CLEANING POWDERS AND METHODS OF USE THEREOF

BACKGROUND AND SUMMARY OF THE INVENTION

The present invention relates to the use of fine powders in a method of cleaning tooth surfaces.

In the context of modern prophylactic treatment it is nowadays customary to remove hard and soft deposits from the hard substance of the tooth by cleaning. To remove the hard deposits, also called congrement or calculus, mechanical techniques, such as scraping with appropriate manual instruments, or the use of ultrasonication tips, are usually employed.

The so-called soft deposits, caused, for example, by consumption of coffee or cigarettes, are generally removed either with polishing pastes or by jet cleaning with a powder/water mixture. Jet cleaning is normally carried out with a mixture of sodium bicarbonate powder in water. This offers the advantage over polishing with pastes that the deposits can be removed much more quickly. A disadvantage, however, is that the powder/water mixtures used are abrasive to the tooth surface, as a result of which the areas of tooth treated become roughened. Consequently, a further workstep becomes necessary, in which the tooth surface must be smoothed again by means of polishing disks. Moreover, abrasiveness of the powder/water mixtures used leads to ablation of the hard substance of the tooth, which in the case of repeated use may lead to sensitivities, particularly in the neck region of the tooth.

GB-A-1 480 594 discloses a method of cleaning tooth surfaces with a water jet containing abrasive substances. Substances said to be suitable include coated or uncoated, organic or inorganic substances. Any indication as to which substances actually make it possible to clean the tooth surface gently and effectively is lacking.

In contrast, German Patent Application 199 10 559 describes the use of fine powders for producing a composition for the powder jet cleaning of root surfaces of teeth, i.e., subgingival tooth surfaces.

It is an object of the present invention to provide powders or powder mixtures for tooth surface cleaning which avoid the problems referred to.

This object is achieved through the use of powders and powder mixtures as described in the claims.

DETAILED DESCRIPTION OF THE INVENTION

Figure 1:
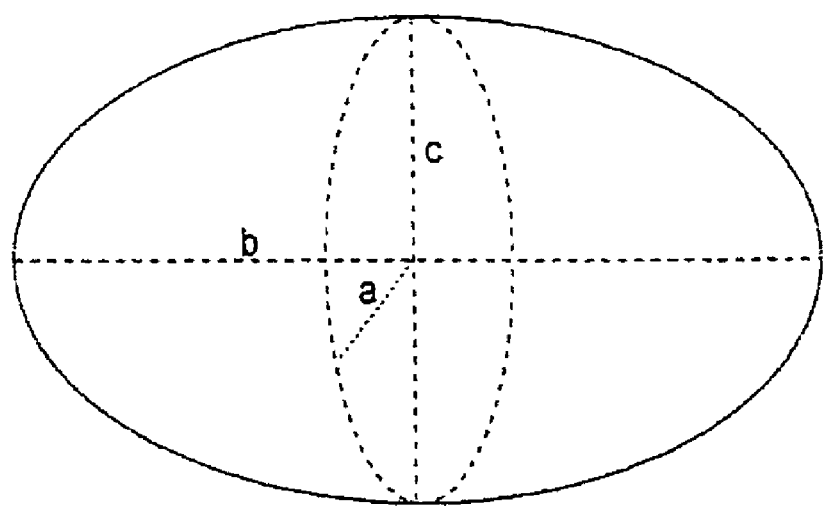
FIG. 1 shows a semiellipsoid for calculating the volume of enamel ablated.

The powders and powder mixtures used in accordance with the invention are such that the abrasion to the supragingival tooth surface caused by powder jet cleaning is not more than 0.10 mm$^3$, preferably not more than 0.08 mm$^3$, with particular preference not more than 0.05 mm$^3$, based on a tooth surface of 9.6 mm$^2$ for a jet cleaning duration of 2 minutes at a jet pressure of 4 bar, and a distance between the tooth surface and jet nozzle of not more than 2.5 mm.

Powders and powder mixtures which can be used in accordance with the invention have a density, for example, of not more than 2.0 g/cm$^3$ and/or have an average particle size of not more than 45 µm.

Powders possessing these properties display a good cleaning action while nevertheless exhibiting no notable abrasiveness toward the supragingival hard substance of the tooth or the visible tooth surface, such as otherwise normally occurs with known compositions.

The abrasiveness is so low that the volume ablation of the supragingival hard substance of the tooth, especially the enamel, is impossible to find, or can be found only to a very minor extent, using duplicating compositions customary in the dental sector (Dimension® Garant from ESPE, for example) and then examining the impression under a light microscope.

As a result, there is no need for a subsequent polishing step.

Additionally, these powders and powder mixtures can be employed repeatedly, even at short intervals, without any notable loss of nonregenerable hard substance of the tooth. These intervals may even amount to just a few days or weeks.

Surprisingly, it has been found that the powders and powder mixtures can be used to remove not only customary contaminations and discolorations of the visible hard substance of the tooth, originating, for example, from nicotine, coffee, tea or red wine colorants, but also plaque residues which are difficult or impossible to see, especially deposits originating from microorganisms.

Because of the preferably small average particle size, the surfaces of the teeth can be cleaned even in interdental areas.

High efficiency in the powder jet cleaning operation is obtained when, for example, the tooth substance is examined for plaque residues, especially invisible plaque residues, before the actual cleaning step. Such deposits on the tooth substance are normally not removed by conventional cleaning of the teeth.

Such deposits can be detected, for example, by using suitable impression compounds, as described in German Patent Application 199 26 728.

The deformable, curable and/or film-forming carrier materials described therein comprise additives which can be utilized diagnostically for site-specific and substance-specific intraoral diagnosis, in a concentration, for example, of from 0.0001 to 10% by weight, preferably in a concentration of from 0.01 to 1% by weight. Examples of diagnostic additives include dye indicators, antibodies, and enzymes. These may be present, where appropriate, in microencapsulated form.

Suitable impression compounds include those, for example, based on polyether, based on silicone, based on hydrocolloid or based on alginate.

Powder and powder mixtures which are suitable for use in the present invention are, in particular, those which can be conveyed by means of conventional powder jet devices for the dental sector.

A feature common to all powders suitable for use in accordance with the invention is that they normally have a lower density than powders and powder mixtures employed to date for supragingival tooth cleaning.

Additionally, they preferably have a small average particle size of not more than 45 µm.

Preference is also given to powders having a particle distribution of from 0.05 µm to 60 µm, and particular preference to those having a particle distribution of from 0.1 µm to 40 µm.

Naturally, powder mixtures comprising at least two powders are also suitable for the purpose described. In such cases the mixing ratio is, in principle, arbitrary, but when using two powders it is preferably in the range from 1:10 to 10:1, based on the mass of the powders to be mixed.

It may also be advantageous to mix the powders with further substances, present in very finely divided form, before using them as cleaning agents for tooth surfaces. This has the effect that the resulting powder mixtures can be conveyed more effectively and more rapidly with conventional powder jet devices.

These substances are customarily added in an amount of from 0.01 to 5.0% by weight, preferably in an amount from 0.5 to 1% by weight.

Examples of such powders present in very finely divided form include boron oxide, silica gel, highly disperse silica, preferably silanized, with organosilanes, such as, for example, silicas containing trimethylsilyl groups.

The fine powders preferably have an average particle size of approximately 0.07 μm, with particular preference of approximately 0.02 μm.

Also conceivable is the admixing of other finely divided substances, examples being bleaches, such as perborates (e.g., sodium perborate), fluoride donor substances, such as sodium fluoride, analgesics, such as articaine or lidocaine, bacteriocides, such as chlorhexidine or triclosan, flavors, such as citric acid or ascorbic acid.

It is preferred to use powders and powder mixtures which are predominantly unobjectionable toxicologically and/or are readily biodegradable both within the body and outside.

Particularly suitable powders for the cleaning of supragingival tooth surfaces are organic substances which occur naturally, such as amino acids, sugars, organic acids and their salts, such as alkali metal salts (e.g., lithium, sodium, potassium), alkaline earth metal salts (e.g., magnesium, strontium) or ammonium salts. Also suitable, however, are inorganic substances provided they exhibit the desired low abrasiveness toward the supragingival hard substance of the tooth and preferably have the described density and particle size.

Glycine, urea, potassium hydrogen phthalate and/or potassium gluconate are particularly advantageous.

The powders may, where appropriate, also have been surface coated. Suitable surface coating agents that may be mentioned include the following: starch, alginates, collagen (gelatin), hydrogels, polyanhydrides, polyesters, polyiminocarbonates, polycaprolactones, polyamino acids, polyphosphazenes.

Suitable powder mixtures are, for example, mixtures of amino acids and sugars and/or organic acids, preferably a mixture of glycine with urea.

Suitable commercially available, nontoxic powders of the desired density and of high purity are normally first ground to the desired particle size in a ball mill or agate disk mill and sieved.

The stated density values correlate to the density values stated by the manufacturers and/or are taken from common reference works. The particle sizes were determined using a granulometer.

Subsequently, where appropriate, further finely divided substances are admixed, followed, where appropriate, by further grinding and further sieving.

The powder mixture obtained is introduced into a commercially available powder jet device and is applied as a jet to the supragingival tooth surface, usually with the aid of a water jet.

Also conceivable, however, is the use of the described powders or powder mixtures for (jet) cleaning dental materials, such as crowns, facings and/or bridges, which are outside the oral cavity.

The use of the described powders and powder mixtures in accordance with the invention preferably takes place in such a way that first of all a diagnostic system, for example, a so-called diagnostic impression compound, as described in German Patent Application 199 26 728, is used to prepare a negative impression of the dentition.

On the basis of this impression it is possible to determine those areas of the tooth substance where there are unwanted deposits, particularly deposits invisible to the human eye, examples being plaque residues and/or microbial degradation products harmful to the tooth substance.

Also conceivable, however, is the application of other diagnosis systems, based on coloring the unwanted deposits, using fluorescent dyes, for example, and their detection. Other diagnostic systems of this kind are described, for example, in DE-A-42 00 741 and DE-A-29 13 415.

This is followed by the cleaning of the hard surface of the tooth, preferably using the powders and powder mixtures described.

Finally, the outcome of cleaning can be checked again, for example, using a so-called diagnostic impression compound.

If cleaning has been unsuccessful, it is possible, where appropriate, for further cleaning of the hard substance of the tooth, using the powders and powder mixtures described, to take place immediately thereafter without notable damage to the hard substance of the tooth.

The invention is illustrated further below with reference to examples:

Preparation of Bovine Teeth and Measurement Procedure:

For each test, three freshly extracted bovine teeth were used, whose enamel region after cleaning by rinsing with deionized water was smoothed superficially by treatment with abrasive paper. The tooth thus prepared was fixed in an investment compound (Permagum®, ESPE, Seefeld) and covered with a metal plate which had a circular cutout with a diameter of 3.5 mm. The exposed area of enamel was subsequently subjected to a jet of the corresponding powder or powder mixture for two minutes by means of a powder jet device (Airflow®, EMS, Munich) with a jet pressure of 4.0 bar and a distance between root surface to jet nozzle of 2.3 mm. For each test, powder tanks each filled to the maximum were used. The device was operated with the setting "powder full" and "water half".

In order to determine the volume of enamel ablated, the jet-cleaned surfaces were duplicated by means of an impression compound (Dimension® Garant, ESPE, Seefeld). The resulting negative of the ablated volume, in the form of a semiellipsoid, was measured along its axes under a light microscope (Zeiss stereomicroscope, 40- to 64-times magnification) and these data were used to calculate the volume ablation by means of the following formula:

$$\text{Ablated volume} = \tfrac{2}{3}\pi a * b * c$$

The semiellipsoid for calculating the volume ablation is depicted in FIG. 1.

EXAMPLE I

Powder Mixture I 100 g of glycine (Fluka, Deisenhofen) were ground for 3 minutes in an agate disk mill and then sieved dry through a 40 μm sieve. The powder thus obtained was then admixed with 0.36 g of HDK-H-2000 (Degussa, Hanau) and this mixture was again sieved through a 60 μm sieve.

EXAMPLE II

Powder Mixture II 100 g of potassium D-gluconate (Fluka, Deisenhofen) were ground for 4 minutes in an agate disk mill and then sieved dry through a 40 μm sieve. The powder thus obtained was then admixed with 0.63 g of HDK-H-2000 (Degussa, Hanau) and this mixture was again sieved through a 60 μm sieve.

EXAMPLE III

Powder Mixture III 100 g of sodium ascorbate (Fluka, Deisenhofen) were ground for 1 minute in an agate disk mill and then sieved dry through a 40 μm sieve. The powder thus obtained was then admixed with 0.9 g of HDK-H-2000 (Degussa, Hanau) and this mixture was again sieved through a 60 μm sieve.

EXAMPLE IV

Reference Example I 100 g of sodium hydrogen carbonate (Fluka, Deisenhofen) were ground for 2.5 minutes in an agate disk mill and then sieved dry through a 40 μm sieve. The powder thus obtained was then admixed with 0.19 g of HDK-H-2000 (Degussa, Hanau) and this mixture was again sieved through a 60 μm sieve.

EXAMPLE V

Reference Example II 100 g of Air-Flow powder (EMS) was used as supplied by the manufacturer.

The powder mixtures I–III thus obtained and also the reference powders I and II were introduced into a powder jet device (Airflow®, EMS, Munich) and used as described above. The respective amount of ablated of tooth substance can be found in Table 1.

TABLE 1

Ablated volume of bovine root dentine as a function of the powder mixture used and its density and average particle size.

| Powder mixture | Density [g/cm$^3$]* | Average particle size [μm]** | Ablated volume [mm$^3$] |
|---|---|---|---|
| I | 1.16 | 10.7 | not measurable |
| II | 1.73 | 21.7 | not measurable |
| III | 1.80 | 21.0 | 0.09 |
| Reference I | 2.16 | 34.8 | 0.13 |
| Reference II | 2.16 | 54.3 | 0.15 |

*Source: Beilstein
**Measured on CILAS granulometer with isopropanol as dispersion medium The volume figure stated in each case in Table 1 is given by the sum of the volumes determined divided by the number of teeth measured.

The invention claimed is:

1. A method of powder jet cleaning supragingival tooth surfaces, comprising:
   providing fine powders or powder mixtures to a powder jet cleaning apparatus wherein said fine powders or powder mixtures are sized such that a tooth surface equal to or less than 0.10 mm$^3$ based on a tooth surface of 9.6 mm$^2$ is abraded; and
   cleaning said supragingival tooth surface with said powder jet cleaning apparatus using a pressure and a duration
   such that abrasion to said supragingival tooth surface by the cleaning method is less than 0.10 mm$^3$ based on a supragingival tooth surface area of 9.6 mm$^2$.

2. A method according to claim 1, wherein said fine powders or powder mixtures have a density of equal to or less than 2.0 g/cm$^3$.

3. A method according to claim 1, wherein said fine powders or powder mixtures have an average particle size of equal to or less than 45 μm.

4. A method according to claim 1, wherein said powder jet cleaning apparatus is a jet pressure device.

5. A method according to claim 1, further comprising admixing a further fine particulate substance to said fine powders or powder mixtures prior to use.

6. A method according to claim 5, wherein said further fine particulate substance is selected from the group consisting of boron oxide, silica gel and silica.

7. A method according to claim 6, wherein said silica is silanized.

8. A method according to claim 1, wherein said fine powders or powder mixtures are selected from the group consisting of amino acids, sugars, organic acids and salts of organic acids.

9. A kit for cleaning tooth surfaces, comprising at least one fine powder or powder mixture and a further substance selected from the group consisting of boron oxide, silica gel, and highly dispersed silica, wherein said fine powder or powder mixture abrades a tooth surface equal to or less than 0.10 mm$^3$ based on a tooth surface of 9.6 mm$^2$ when said fine powder or powder mixture is applied to said tooth surface using a jet cleaner for 2 minutes at a pressure of 4 bar with said jet cleaner equal to or less than 2.5 mm from said tooth surface and wherein said fine powder or powder mixture has a density of equal to or less than 2.0 g/cm$^3$ and an average particle size of equal to or less than 45 μm.

10. A kit according to claim 9, further comprising a system for detecting at least one of contamination or deposits on said tooth surface.

11. A kit according to claim 9, wherein said fine powder or powder mixture has an average particle size of equal to or less than 45 μm.

12. A kit according to claim 9, further comprising an impression compound.

13. A tooth cleaning device, comprising:
   a jet pressure device; and
   a fine powder or powder mixture,
   wherein said fine powder or powder mixture is sized such that a tooth surface equal to or less than 0.10 mm$^3$ based on a tooth surface of 9.6 mm$^2$ is abraded when said fine powder or powder mixture is applied to said tooth surface using a jet cleaner for 2 minutes at a pressure of 4 bar with said jet cleaner equal to or less than 2.5 mm from said tooth surface and wherein said fine powder or powder mixture has a density of equal to or less than 2.0 g/cm$^3$.

14. A tooth cleaning device according to claim 13, wherein said fine powder or powder mixture has an average particle size of equal to or less than 45 μm.

15. A tooth cleaning powder comprising a substance selected from the group consisting of boron oxide, silica gel, and highly dispersed silica and a plurality of fine particles having an average particle size of equal to or less than 45 μm and a density of equal to or less than 2.0 g/cm³.

16. A tooth cleaning powder according to claim 15, wherein said fine particles have a size distribution between 0.5 μm and 60 μm.

17. A tooth cleaning powder according to claim 15, further comprising a diagnostic additive.

18. A tooth cleaning powder according to claim 17, wherein said diagnostic additive is selected from the group consisting of dye indicators, antibodies, and enzymes.

19. A tooth cleaning powder according to claim 15, wherein said highly dispersed silica is silanized with organosilanes.

20. A tooth cleaning powder according to claim 15, wherein said further substance comprises 0.01 to 5.0% of the tooth cleaning powder by weight.

21. A tooth cleaning powder according to claim 15, wherein said further substance comprises 0.5 to 1.0% of the tooth cleaning powder by weight.

22. A tooth cleaning powder according to claim 15, wherein said further substance has an average particle size of 0.07 μm.

23. A tooth cleaning powder according to claim 15, wherein said further substance has an average particle size of 0.02 μm.

24. A tooth cleaning powder according to claim 15, further comprising a substance selected from the group consisting of bleaches, fluoride donor substances, analgesics, bacteriocides, and flavors.

25. A tooth cleaning powder according to claim 15, wherein said fine particles comprise organic substances.

26. A tooth cleaning powder according to claim 25, wherein said organic substances are selected from the group consisting of amino acids, sugars, organic acids, and salts of organic acids.

27. A tooth cleaning powder according to claim 15, wherein said fine particles comprise a substance selected from the group consisting of glycine, urea, potassium hydrogen phthalate, and potassium gluconate.

28. A tooth cleaning powder according to claim 15, wherein said fine particles have a surface coating.

29. A tooth cleaning powder according to claim 28, wherein said surface coating is selected from the group consisting of starch, alginates, collagen, hydrogels, polyanhydrides, polyesters, polyiminocarbonates, polycaprolactones, polyamino acids, and polyphosphazenes.

* * * * *

UNITED STATES PATENT AND TRADEMARK OFFICE
CERTIFICATE OF CORRECTION

PATENT NO. : 7,083,411 B2
APPLICATION NO. : 10/239647
DATED : August 1, 2006
INVENTOR(S) : Thomas Flemmig It is certified that error appears in the above-identified patent and that said Letters Patent is hereby corrected as shown below:

Column 7
Line 15, in Claim 20, after "said" delete "further".
Line 18, in Claim 21, after "said" delete "further".
Line 21, in Claim 22, after "said" delete "further".
Line 24, in Claim 23, after "said" delete "further".

Signed and Sealed this

Twentieth Day of May, 2008

JON W. DUDAS
*Director of the United States Patent and Trademark Office*